United States Patent [19]

Passarelli

[11] Patent Number: 4,933,175

[45] Date of Patent: Jun. 12, 1990

[54] PROCESS AND PRODUCT FOR PREPARING HUMAN NAIL STRENGTHENING COMPOSITION

[75] Inventor: Michael A. Passarelli, Hoffman Estate, Ill.

[73] Assignee: de'jeuner, Inc., Wauwatosa, Wis.

[21] Appl. No.: 225,282

[22] Filed: Jul. 28, 1988

[51] Int. Cl.$^5$ ............................................. A61K 7/04
[52] U.S. Cl. ..................................... 424/61; 514/769; 514/772; 514/787; 514/789
[58] Field of Search .................. 424/61; 514/769, 772, 514/787, 789

[56] References Cited

U.S. PATENT DOCUMENTS 4,530,828 7/1985 Smith et al. .......................... 424/61

Primary Examiner—Thurman K. Page
Assistant Examiner—Susan S. Rucker
Attorney, Agent, or Firm—Andrus, Sceales, Starke & Sawall

[57] ABSTRACT

An improved composition and process for preparing the composition is provided for strengthening and hardening human fingernails and toenails. A base composition comprising lanolin, unsalted butter, beeswax, rosin, copper acetate, turpentine is mixed with titanium dioxide, mineral oil and fragrance.

6 Claims, No Drawings

PROCESS AND PRODUCT FOR PREPARING HUMAN NAIL STRENGTHENING COMPOSITION

BACKGROUND OF THE INVENTION

This invention relates to a process of preparing a composition having particular application in strengthening and hardening of human fingernails and toenails.

With recent renewed interest in health care, physical appearance and general well being, there has been particular emphasis on the appearance of hair, skin and fingernails. Not only has there been an increase in the number of manicure facilities, but these facilities have become "salons" for the health, well-being and beautification of fingernails and toenails. In this respect, a very important area of the beauty treatment industry has been the advent of fingernail salons in conjunction with hair salons and "stand alone" nail treatment salons. Particular attention has been directed to treatment of fingernails and toenails to both harden and strengthen the nails to prevent or minimize breaking, cracking, splitting and peeling.

SUMMARY OF THE INVENTION

The invention provides a product and a process for the preparation of a product for application to human fingernails and toenails for hardening and strengthening the nails. The composition stems from a known composition used for many years to prevent and heal quarter cracks while increasing the growth of hooves of thoroughbred race horses. Human fingernails and toenails are of similar protein consistency to that of horses hooves. However, several drawbacks to using the horse composition for human beings were readily apparent. It is not necessary to harden the human fingernail or toenail to the same degree as that necessary for a horse's hoof. The prior composition has an unacceptable odor, or at least an odor that would not be acceptable for human consumption.

By way of background, the known formula for use in hardening and strengthening horse's hooves comprised the following components: lanolin, unsalted butter, beeswax, natural rosin, copper acetate and turpentine. A preferred composition mixture known to be useful for the past many years contained a mixture prepared as follows:
lanolin - 3 pounds
unsalted butter - 3 pounds
beeswax - 3 pounds
rosin - 3 pounds
copper acetate - 1 pound
turpentine - 1 pint.

In the process for preparing the preferred composition for treatment of horses hooves the consistency of the basic composition is of a compliant "gel" suitable for packaging and storage purposes. The ingredients are admixed and heated to a "simmer" stage and continuously stirred for packaging, after which the gel forms. In use, a predetermined amount of the candle-like gel is removed from the package and melted to a liquid consistency and applied directly to the hoof of the horse by scrubbing the material into the hoof with a hard brush.

The present invention takes advantage of the known base composition. To the base composition there is added additional ingredients including titanium oxide, mineral oil and a desirable fragrance suitable for human use.

DETAILED DESCRIPTION OF THE PREFERRED EMBODIMENT

As stated previously, a preferred embodiment of the process and product of this invention utilizes the known composition found to be useful for many years in treatment for strengthening and hardening of horses' hooves ("Base Composition"). An additive composition containing ingredients for improving the base composition for use in human consumption is admixed therewith.

The improved product includes the aforementioned Base Composition with ingredients in the amounts disclosed above, i.e. lanolin - 3 pounds; unsalted butter - 3 pounds; beeswax - 3 pounds; rosin - 3 pounds; copper acetate - 1 pound; turpentine - 1 pint.

To the Base Composition is added the "Additive Composition" comprising titanium oxide ($TiO_2$) - 7% by weight of the Base Composition; mineral oil - 15% by weight of the Base Composition; and a fragrance known as J-5402, obtained from Bell Flavors and Fragrances, Northbrook, Illinois - 3% by weight of Base Composition.

For example, a very suitable hardening and strengthening media for human nails may be prepared as follows.

10 pounds of Base Composition is mixed with 2 1/2 pounds of Additive Composition to provide a total composition having 80% by weight of Base Composition and 20% by weight of Additive Composition.

The Additive Composition portion comprises:
0.7 pounds (11.2 ounces) Titanium Dioxide ("TI-PURE R900" obtained from E.I. duPont)
1.5 pounds (24 ounces) of common mineral oil
0.3 pounds (4.8 ounces) of fragrance extract (J-5402).

The mixture was heated with continual stirring to a "simmer" stage (not a rolling boil), and poured into suitable containers for storage and use.

The two-stage example has been set forth for illustrative purposes only. As mentioned earlier the Base Composition is known, and for convenience, the readily obtainable Pre-mixed Base Composition was used with the Additive Composition being added thereto after melting the "candle-like" Base material. However, the present invention further contemplates admixing all ingredients (both Base and Additive Compositions) at the same time and simmering them together with continued stirring, and then pouring the mix into suitable containers for storage and use.

The improved strengthening and hardening composition was subjected to market research by an unbiased panel which found that the composition not only improves nail growth, hardening and strengthening, but also minimizes breaking, cracking, splitting and healing. Members of the panel simply applied small amounts to the cuticle of the fingernail and the nail itself, preferably at bedtime. The product was massaged thoroughly into the entire nail and cuticle area for 10-15 seconds per nail. This process was repeated nightly for two weeks, and then twice a week thereafter.

After one month, tabulation of the results indicated improvement in the prevention of nail splitting, nail breaking, nail chipping, strengthening of the nails and improvement of appearance of the cuticles.

Various modifications and variations to the preferred embodiment, but which will still embody the spirit of the invention, will be apparent to those skilled in the art. Therefore, the invention is not intended to be limited by the scope of the preferred embodiment, but only by the claims which follow, except as otherwise required by law.

What I claim is:

1. A process for preparing a nail strengthener for human fingernails and toenails, comprising the steps of admixing lamolin, unsalted butter, beeswax, rosin, copper acetate, and turpentine to form a first mixture, and adding to said first mixture titanium dioxide, mineral oil and a fragrance; heating the mixture at a simmering temperature with stirring whereby said titanium dioxide, mineral oil and fragrance combine with the ingredients of said first mixture to yield a final mixture having a color and odor satisfactory for human use, and cooling said mixture.

2. The process of claim 1, wherein the ingredients comprise:

| | | | |
|---|---|---|---|
| Lanolin | Approx. | 3 | pounds |
| Unsalted Butter | Approx. | 3 | pounds |
| Beeswax | Approx. | 3 | pounds |
| Rosin | Approx. | 3 | pounds |
| Copper Acetate | Approx. | 1 | pound |
| Turpentine | Approx. | 1 | pint |
| Titanium Dioxide | Approx. | 0.7 | pounds |
| Mineral Oil | Approx. | 1.5 | pounds |
| Fragrance | Approx. | 0.3 | pounds. |

3. The process of claim 1 wherein the admixture consists essentially of approximately 80% by weight of said first mixture and approximately 20% by weight of said titanium dioxide, mineral and fragrance.

4. A human nail strengthening composition comprising a first mixture of lanolin, unsalted butter, beeswax, rosin, copper acetate, and turpentine, and a second mixture of titanium dioxide, mineral oil and a fragrance added to said first mixture, wherein said second mixture combines with said first mixture to yield a final mixture having a color and odor satisfactory for human use.

5. The composition of claim 4, wherein the mixture comprises approximately 80% by weight of said first mixture and 20% by weight of said second mixture.

6. A human nail strengthening composition comprising a mixture including the following:

| | | | |
|---|---|---|---|
| Lanolin | Approx. | 3 | pounds |
| Unsalted Butter | Approx. | 3 | pounds |
| Beeswax | Approx. | 3 | pounds |
| Rosin | Approx. | 3 | pounds |
| Copper Acetate | Approx. | 1 | pound |
| Turpentine | Approx. | 1 | pint |
| Titanium Dioxide | Approx. | 0.7 | pounds |
| Mineral Oil | Approx. | 1.5 | pounds |
| Fragrance | Approx. | 0.3 | pounds. |

* * * * *